United States Patent [19]

Acharya et al.

[11] Patent Number: 5,585,484
[45] Date of Patent: Dec. 17, 1996

[54] HEMOGLOBIN CROSSLINKERS

[75] Inventors: A. Seetharama Acharya; Belur N. Manjula, both of Cresskill, N.J.; Paul K. Smith, Roscoe, Ill.

[73] Assignee: Albert Einstein College of Medicine of Yeshiva University, A Division of Yeshiva University, Bronx, N.Y.

[21] Appl. No.: 425,137

[22] Filed: Apr. 19, 1995

[51] Int. Cl.$^6$ .................................................. A61K 31/40
[52] U.S. Cl. ........................... 540/145; 548/521; 548/549
[58] Field of Search ........................... 540/145; 514/6, 514/422, 425; 548/521, 549

[56] References Cited

U.S. PATENT DOCUMENTS

| | | | |
|---|---|---|---|
| 4,179,337 | 12/1979 | Davis et al. | 435/181 |
| 4,301,144 | 11/1981 | Iwashita et al. | 424/78 |
| 4,412,989 | 11/1983 | Iwashita et al. | 424/177 |
| 4,609,546 | 9/1986 | Hiratani | 424/83 |
| 5,122,614 | 6/1992 | Zalipsky | 514/6 |
| 5,234,903 | 8/1993 | Nho et al. | 514/6 |
| 5,312,808 | 5/1994 | Shorr et al. | 514/6 |
| 5,386,014 | 1/1995 | Nho et al. | 530/385 |

FOREIGN PATENT DOCUMENTS

| | | |
|---|---|---|
| 9404193 | 3/1994 | WIPO . |
| 9409027 | 4/1994 | WIPO . |

OTHER PUBLICATIONS

Walder, R., et al. *Method in Enzymology* 231:274–288 (1994).

Bunn, H. F. *American Journal of Hematology* 42:112–117 (1993).

Razynska, H., et al. *FASEB* Abstract No. 578 (1994).

Manjula, B. N., et al. *Art. Cells, Blood Subs., And Immob Biotech*, 22(3) 747,752 (1994).

Nho, K., et al., *Art. Cells, Blood Subs., And Immob. Biotech*, 22(3), 795–803 (1994).

Annunziato, M., et al. *Bioconjugated Chem.* 4:212–281 (1993).

Simon, S. R. and W. H. Konigsberg *Biochemistry* 56:749–756 (1966).

Bunn, H. F., et al. *J. Exp. Med.* 129:909–924 (1969).

Xue, H. and J.T.–F. Wong *Methods in Enzymology* 231:308–322 (1994).

MacDonald, S. L. and D. S. Pepper *Methods in Enzymology* 231:287–280 (1994).

Kluger, R., et al. *Art. Cells, Blood Subs., and Immob. Biotech.* 22(3):415–428 (1994).

*Primary Examiner*—Joseph McKane
*Attorney, Agent, or Firm*—Amster, Rothstein & Ebenstein

[57] ABSTRACT

The present invention provides a class of compounds having the formula:

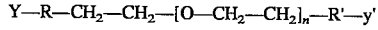

wherein n is an integer from about 5 to about 200; R is carbamate, urea, or amide; R' is carbamate, urea, amide, or oxygen; Y is 4-phenylmalemimido or 3-phenylmaleimido; and Y' is 4-phenylmalemimido, 3-phenylmaleimido, methyl or hydrogen. The present invention also provides various hemoglobin compositions modified with the class of compounds of the present invention, processes for preparing these compositions, as well as pharmaceutical compositions comprising these compositions.

15 Claims, 9 Drawing Sheets

ANALYSIS OF PEG 2000 REACTED HEMOGLOBIN

INTRAMOLECULAR CROSSBRIDGING OF HbA BY BIS MAL PEG 5000

HEMOGLOBIN CROSSLINKERS

BACKGROUND OF THE INVENTION

Hemoglobin (Hb) is the major constituent of the erythrocyte which carries oxygen from the lungs throughout the body. When contained in red blood cells, Hb exists as a tetramer structure composed of two oxygen linked αβ dimers each having a molecular weight of about 32 Kd. Each α and β subunit of each dimer has a protein chain and a heme molecule. The sequences of the α and β protein chains are known. Hb is a potentially useful blood substitute for transfusions, and has been proposed as a reagent to trap nitric oxide in septic shocks, and to modulate tissue oxygenation during the radiation therapy of cancer. Recombinant DNA technology also has afforded the generation of modified Hb with oxygen affinities modulated for special needs of individual therapeutic applications.

The potential use of Hb as blood substitutes in transfusions or other therapeutic applications, however, has been hampered by the short circulation half-life of Hb. In solution outside of the red blood cell, Hb readily dissociates from its tetrameric form into its dimers and even monomers, which are rapidly filtered through the kidneys. Accordingly, a multitude of methods for crossbridging Hb (e.g. bifunctional modification) and other means for increasing the hydrodynamic volume of Hb (e.g. monofunctional decoration) have been devised to limit or prevent the extravasation of Hb.

Simon, S. R. and Konigsberg, W. H. reported the use of bis(N-maleimidomethyl) ether (BME) to generate intra-crosslinked Hb (*Proc. Natl. Acad. Sci.* 56:749–756 (1966). Bunn, H. F., et al. later reported that BME crosslinked Hb increased the half-life of Hb four-fold when infused into rats and dogs (*J. Exp. Med.* 129:909–924 (1969)). However, the crosslinking of Hb with (BME) resulted in a concomitant increase in the oxygen affinity of Hb which prevented its use as a potential Hb-based oxygen carrier.

Xue, H. and Wong, J. T.-F. described many of the current methods for crosslinking Hb (*Methods in Enzymology* 231:308–322 (1994)). These include the use of dextran, hydroxyethyl starch, inulin, polyvinylpyrrolidone, and polyethylene glycol as crosslinkers for Hb. Other crosslinkers include glutaraldehyde (MacDonald, S. L. and Pepper, D. S. *Methods in Enzymology* 231:287–308 (1994)); bis(3,5-dibromosalicyl) fumarate (Walder, R. Y., et al. *Methods in Enzymology* 231:274–281 (1994)); acyl phosphate esters (Kluger, R., et al. *Art. Cells, Blood Subs., and Immob. Biotech.* 22(3): 415–428 (1994) and U.S. Pat. No. 5,334,707); bissulfosuccinimidyl esters of aliphatic dicarboxylic acids (Manjula, B. N., et al. *Art. Cells, Blood Subs., and Immob. Biotech.* 22(3): 747–752 (1994)); and benzenepentacarboxylate (U.S. Pat. No. 5,349,054).

Nho, K. et al. described the monofunctional decoration of hemoglobin with polyethylene glycol (*Art. Cells, Blood Subs., and Immob. Biotech.* 22(3): 795–803 (1994)). Similar modification of the hemoglobin molecule are described in U.S. Pat. Nos. 4,670,417, 5,234,903, and 5,312,808.

Most of the known compounds used to modify Hb are difficult to synthesize, do not modify Hb in an efficient manner, cannot be manipulated quantitatively to form the desired modification, or lower or raise the oxygen affinity of the modified hemoglobin. Accordingly, there exists a need for new compounds which are easily synthesized, modify hemoglobin in an efficient and focused manner, and do not substantially affect the oxygen affinity of the modified hemoglobin. The present invention satisfies this need.

SUMMARY OF THE INVENTION

The present invention provides a compound having the formula:

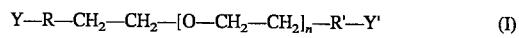

$$Y-R-CH_2-CH_2-[O-CH_2-CH_2]_n-R'-Y' \quad (I)$$

wherein n is an integer from about 5 to about 200; R is carbamate, urea, or amide; R' is carbamate, urea, amide, or oxygen; Y is 4-phenylmalemimido or 3-phenylmaleimido; and Y' is 4-phenylmalemimido, 3-phenylmaleimido, methyl or hydrogen. The present invention also provides an intra-crosslinked hemoglobin composition having the formula:

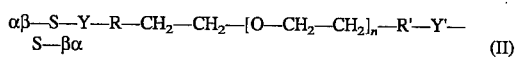

$$\alpha\beta-S-Y-R-CH_2-CH_2-[O-CH_2-CH_2]_n-R'-Y'- \\ S-\beta\alpha \quad (II)$$

wherein n is an integer from about 5 to about 200; R and R' are carbamate, urea, or amide; and Y and Y' are 4-phenylsuccinimido or 3-phenylsuccinimido.

The present invention further provides an inter-crosslinked hemoglobin composition having the formula:

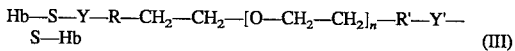

$$Hb-S-Y-R-CH_2-CH_2-[O-CH_2-CH_2]_n-R'-Y'- \\ S-Hb \quad (III)$$

wherein n is an integer from about 5 to about 13; R and R' are carbamate, urea, or amide; and Y and Y' are 4-phenylsuccinimido or 3-phenylsuccinimido.

The present invention still further provides a hemoglobin composition having the formula:

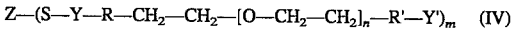

$$Z-(S-Y-R-CH_2-CH_2-[O-CH_2-CH_2]_n-R'-Y')_m \quad (IV)$$

wherein n is an integer from about 5 to about 200; m is an integer from about 2 to about 16; R is carbamate, urea, or amide; R' is carbamate, urea, amide, or oxygen; Y is 4-phenylsuccinimido or 3-phenylsuccinimido; Y' is methyl or hydrogen; and Z is Hb or an αβ dimer of Hb.

Additional objects of the present invention will be apparent from the description which follows.

BRIEF DESCRIPTION OF THE FIGURES

FIG. 2 is comprised of FIGS. 2A and 2B, and represents analysis of the Bis-Mal-PEG 2000 modified Hb on FPLC and RPHPLC.

DETAILED DESCRIPTION OF THE INVENTION

Figure 1A:
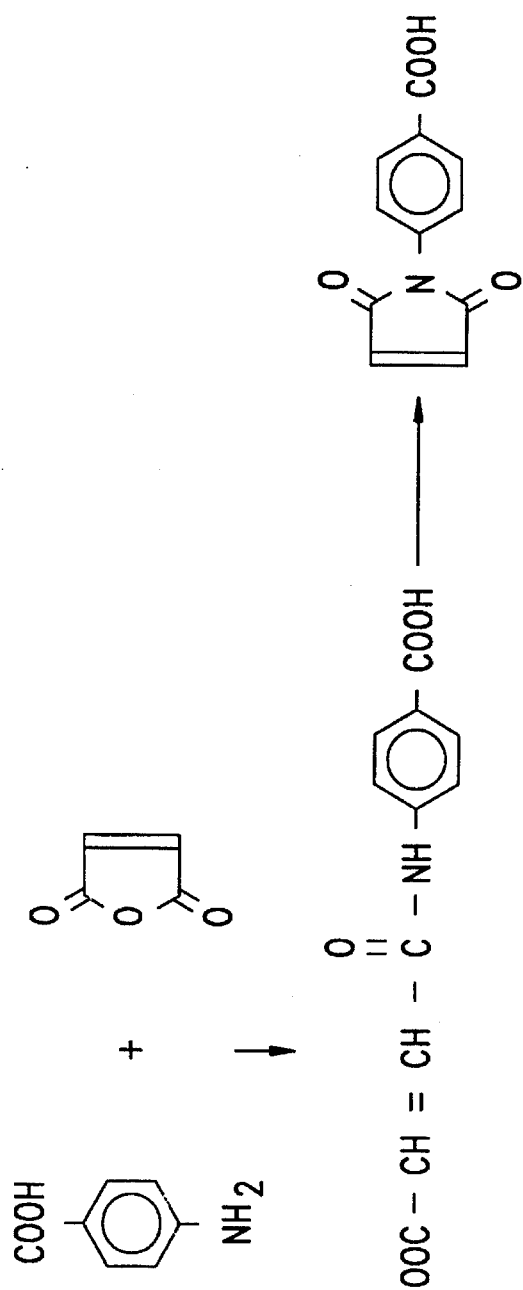
FIG. 1 represents a schematic diagram of the synthesis of para-maleimidobenzoic acid (I), para-maleimidobenzolyazide (II), para-maleimidophenyl isocyanate (III), and bis-maleimidophenyl carbamate of polyethylene glycol (IV).
Figure 1B:
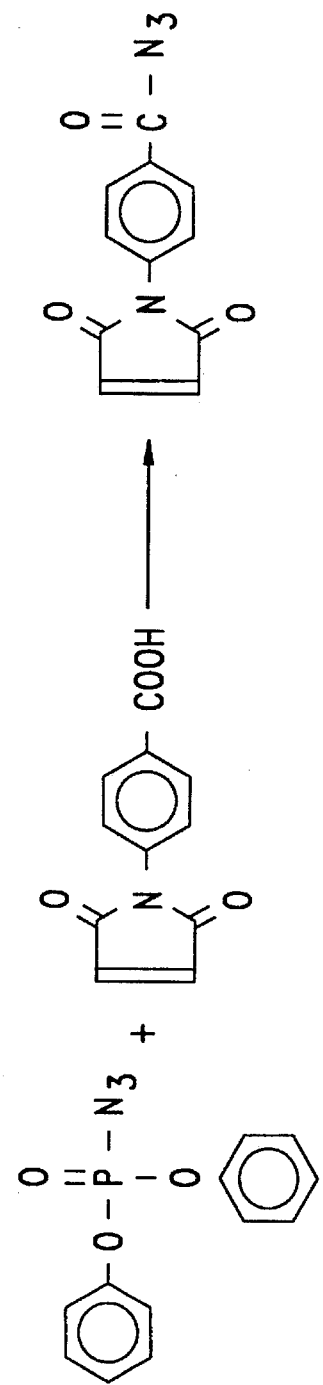
Figure 1C:
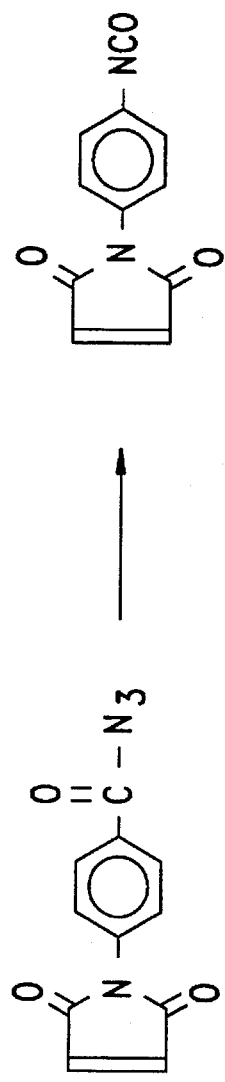
Figure 1D:
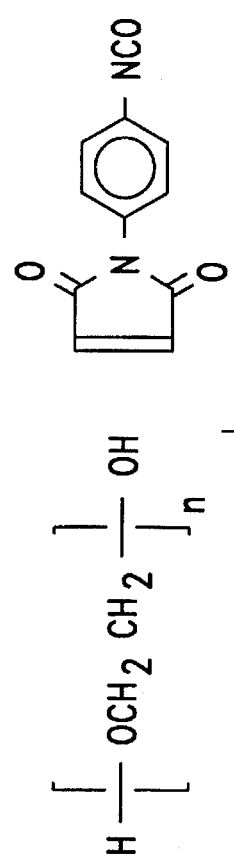
Figure 1D:
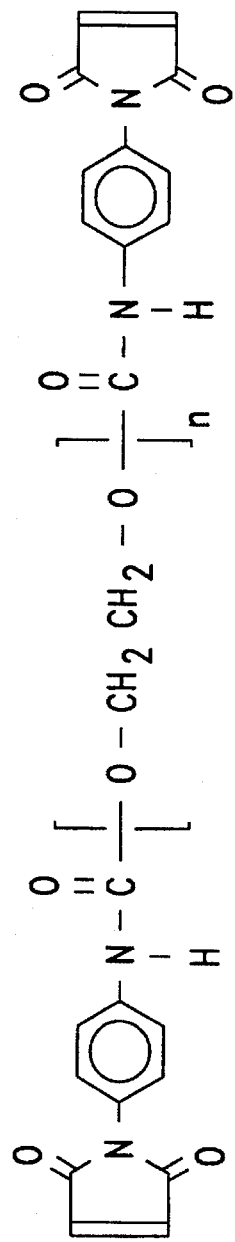

The present invention provides a class of compounds having the formula:

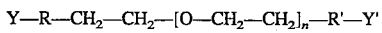  (I)

wherein n is an integer from about 5 to about 200; R is carbamate, urea, or amide; R' is carbamate, urea, amide, or oxygen; Y is 4-phenylmalemimido or 3-phenylmaleimido; and Y' is 4-phenylmalemimido, 3-phenylmaleimido, methyl or hydrogen. Preferred compounds include: (Ia) Y and Y' are 4-phenylmaleimido, and R and R' are carbamate; and (Ib) Y is 4-phenylmaleimido, Y' is methyl, R is carbamate, and R' is oxygen, and may be represented by the formulae:

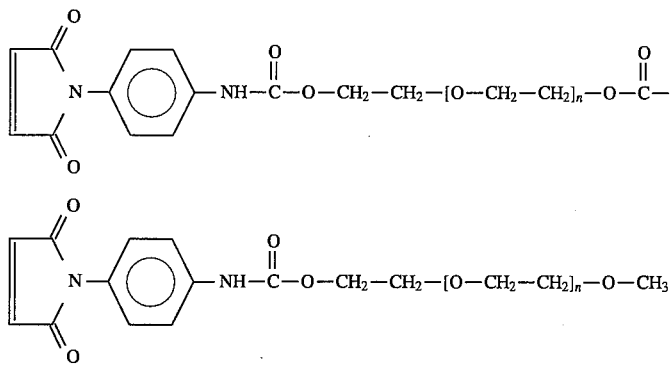

In the particularly preferred embodiment of compound Ia, n is 13, 45, and 75. Such compounds have been designated as Bis-Mal-PEG 600, Bis-Mal-PEG 2000, and Bis-Mal-PEG 3400, respectively. In the particularly preferred embodiment of compound Ib, n is 125. Such compound has been designated as Mal-PEG 5000.

The compounds of the present invention may be synthesized from 4- or 3-maleimidophenyl isocyanate prepared as described in Annunziato, M. E., et al. *Bioconjugate Chem.* 4:212–218 (1993) from commercially available starting materials. Polyethylene glycols of various lengths having each terminus substituted with either a hydroxy function and/or a primary amine function are commercially available from Aldrich Chemical Co., Milawaukee, Wis., and Shearwater Polymers, Inc., Huntsville, Ala.

Compounds having the formula above wherein Y and Y' are 4- or 3-phenylmalemido and R and R' are carbamate may be prepared by reacting PEG-$(OH)_2$ of chosen length dissolved in a dry aprotic solvent such as toluene and an equivalent amount of 4- or 3-maleimidophenyl isocyanate. Addition of the isocyanate to terminal hydroxy groups of PEG is nearly spontaneous yielding a stable carbamate linkage. Using about half the amount of 4- or 3-phenylmalemido isocyanate would yield hydroxy, malemidophenyl carbamate linked PEG (wherein Y is 4- or 3-phenylmaleimido, Y' is hydrogen, R is carbamate, and R' is oxygen). Substitution of PEG($OCH_3$)(OH) for PEG$(OH)_2$ would yield methoxy, malemidophenyl carbamate linked PEG (wherein Y is 4- or 3-phenylmaleimido, Y' is methyl, R is carbamate, and R' is oxygen).

Compounds having the formula above wherein Y and Y' are 4- or 3-phenylmalemido and R and R' are urea may be prepared by reacting PEG-$(NH)_2$ of chosen length dissolved in a dry aprotic solvent such as toluene and an equivalent amount of 4- or 3-maleimidophenyl isocyanate. Using about half the amount of 4- or 3-phenylmalemido isocyanate would yield hydroxy, malemidophenyl urea linked PEG (wherein Y is 4- or 3-phenylmaleimido, Y' is hydrogen, R is urea, and R' is oxygen). Substitution of PEG($OCH_3$)(NH) for PEG$(NH)_2$ would yield methoxy, malemidophenyl urea linked PEG (wherein Y is 4- or 3-phenylmaleimido, Y' is methyl, R is urea, and R' is oxygen).

Compounds having the formula above wherein Y and Y' are 4- or 3-phenylmalemido and R and R' are amine may be prepared by reacting an aqueous solution of PEG-$(NH)_2$ of chosen length dissolved with an excess of the commercially available 4- or 3-maleimidobenzoic acid, N-hydroxysuccinimide ester (MBS) in the presence of dissolved sodium bicarbamate. Although MBS is insoluble in water and is slowly hydrolyzed, it is solubilized during the reaction as amide bonds are formed with the amine containing PEG. Using half the amount of 4- or 3-maleimidobenzoic acid, N-hydroxsuccinimide ester (MBS) would yield hydroxy, malemidophenyl amine linked PEG (wherein Y is 4- or 3-phenylmaleimido, Y' is hydrogen, R is amine, and R' is oxygen). Substitution of PEG($OCH_3$)(NH) for PEG$(NH)_2$ would yield methoxy, malemidophenyl amine linked PEG (wherein Y is 4- or 3-phenylmaleimido, Y' is methyl, R is amine, and R' is oxygen).

The compounds of the present invention are particularly useful for the intra- or inter-crosslinking of hemoglobin, as well as the decoration of Hb with chains to increase the hydrodynamic volume of Hb. As used herein, "Hb" is defined as hemoglobin obtained from human beings; animals such as cattle, swine, sheep, horses, monkeys, chickens, and the like; recombinantly produced hemoglobin; as well as modified versions of the hemoglobins provided above, which include but are not limited to modifications increasing or decreasing the oxygen affinity of hemoglobin.

Accordingly, the present invention also provides an intra-crosslinked hemoglobin composition having the formula:

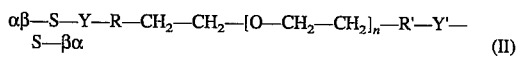
$$\alpha\beta-S-Y-R-CH_2-CH_2-[O-CH_2-CH_2]_n-R'-Y'-S-\beta\alpha \quad (II)$$

wherein n is an integer from about 5 to about 200; R and R' are the same or different and are carbamate, urea, or amide; and Y and Y' are the same or different and are 4-phenylsuccinimido or 3-phenylsuccinimido. As used above, each αβ refers to a dimer of Hb, and each S refers to the sulfur which makes up the thiol group contained on each β subunit. In the preferred embodiment, Y and Y' are 4-phenylsuccinimido, and R and R' are carbamate. The preferred composition may be represented by the formula:

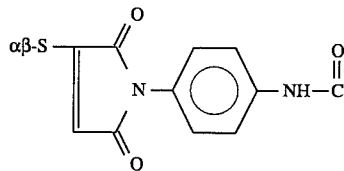

In the particularly preferred embodiment, n is 13, 45, or 75.

The intra-crosslinked hemoglobin composition may be prepared by reacting Hb with the compound having the formula:

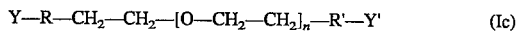
$$Y-R-CH_2-CH_2-[O-CH_2-CH_2]_n-R'-Y' \quad (Ic)$$

wherein n is an integer from about 5 to about 200; R and R' are carbamate, urea, or amide; and Y and Y' are 4-phenylmalemimido or 3-phenylmaleimido. It is preferred that the compound is present in about a two-fold molar excess over the Hb concentration. The concentration of Hb is typically about 0.1 mM to about 3.0 mM, and most preferably about 0.5 mM; the concentration of the compound is typically about 0.2M to about 6.0 mM, and most preferably about 1.0 mM. Higher or lower concentrations of the components may be used. The reaction should be performed for about 0.25 to about 3 hours, and preferably about 1 hour, at room temperature, at pH about 6.5–8.5, and preferably neutral pH.

The reaction may also be carried out at about 4° C. overnight if desired.

The progress of the linking reaction may be followed by FPLC analysis of the sample on a Pharmacia Superose-12 Column, equilibrated and eluted with 1M $MgCl_2$ in 50 mM bis tris buffer, pH 7.0. The uncrosslinked material dissociates into αβ dimers and elutes with an apparent molecular weight of 32 Kd. The intra-crosslinked Hb elutes at the position of Hb with an apparent molecular weight of 64 Kd.

The intra-crosslinked Hb composition may be purified by ion exchange chromatography. Preferably, a CM-52 column (0.9×30 cm for a load of 200 to 500 mg of lots of Hb reaction mixture) equilibrated with 10 mM potassium phosphate buffer, pH 6.5 is used. The chromatogram is developed using a linear gradient generated from 250 ml each of 10 mM phosphate buffer pH 6.5, and 15 mM phosphate buffer pH 8.5. The intramolecularly crosslinked Hb elutes slightly ahead of the position of Hb from these columns. The chromatographic fractions containing the crosslinked species are then pooled, and concentrated by standard techniques.

The present invention also provides an inter-crosslinked hemoglobin composition having the formula:

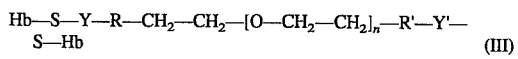
$$Hb-S-Y-R-CH_2-CH_2-[O-CH_2-CH_2]_n-R'-Y'-S-Hb \quad (III)$$

wherein n is an integer from about 5 to about 13; R and R' are the same or different and are carbamate, urea, or amide; and Y and Y' are the same or different and are 4-phenylsuccinimido or 3-phenylsuccinimido. As used above, each Hb is "hemoglobin" which has been intra-crosslinked using the intra-crosslinker of the present invention or other crosslinkers known in the art which include but are not limited to dibromo salicyl fumarate, dibromo salicyl sebacate, bis-sulfosuccinimidyl suberate, and sebacate. Each S refers to the sulfur which makes up the thiol group contained on one of the β subunits of the Hb dimer. In the preferred embodiment, Y and Y' are 4-phenylsuccinimido, and R and R' are carbamate. The preferred composition may be represented by the formula:

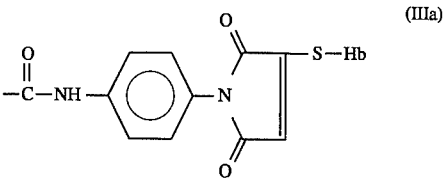

In the particularly preferred embodiment, n is 13.

The inter-crosslinked hemoglobin composition may be prepared by reacting Hb with the compound having the formula:

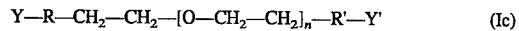
$$Y-R-CH_2-CH_2-[O-CH_2-CH_2]_n-R'-Y' \quad (Ic)$$

wherein n is an integer from about 5 to about 13; R and R' are carbamate, urea, or amide; and Y and Y' are 4-phenylmalemimido or 3-phenylmaleimido. The compound is preferably present in about at least a two-fold molar excess over the Hb concentration. Typical concentrations of Hb range from about 1.5 mM to about 3.0 mM, and preferably about 2.5 mM; for the compound, about 3.0 mM to about 6.0 mM, and preferably about 5.0 mM. The reaction should be performed for about 0.25 to about 3 hours, and preferably about 1 hour, at room temperature, at pH about 6.5–8.5, and preferably neutral pH. The reaction may also be carried out at about 4° C. overnight if desired. The progress of the linking reaction as well as the subsequent purification may be performed as described above. The inter-crosslinked material elutes with an apparent molecular weight of 128 Kd.

The present invention also provides a hemoglobin composition having the formula:

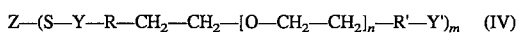

$$Z-(S-Y-R-CH_2-CH_2-[O-CH_2-CH_2]_n-R'-Y')_m \quad (IV)$$

wherein n is an integer from about 5 to about 200; m is an integer from about 2 to about 16; R is carbamate, urea, or amide; R' is carbamate, urea, amide, or oxygen; Y is 4-phenylsuccinimido or 3-phenylsuccinimido; Y, is methyl or hydrogen; and Z is Hb or an αβ dimer of Hb. As used above, each Hb is "hemoglobin" which has been intra-crosslinked using the intra-crosslinker of the present invention or other crosslinkers known in the art which include but are not limited to dibromo salicyl fumarate, dibromo salicyl sebacate, bis-sulfosuccinimidyl suberate, and sebacate. αβ refers to a dimer of Hb. Each S refers to the sulfur which makes up the thiol group contained on one of the B subunits of the Hb dimer. In the preferred embodiment, Y is 4-phenylsuccinimido, Y, is methyl, R is carbamate, and R' is oxygen, and most preferably, n is 25, and m is 8.

The hemoglobin composition (when m is about 2) may be prepared by reacting Hb with the compound having the formula:

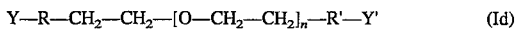

$$Y-R-CH_2-CH_2-[O-CH_2-CH_2]_n-R'-Y' \quad (Id)$$

wherein n is an integer from about 5 to about 200; R is carbamate, urea, or amide; R' is carbamate, urea, amide, or oxygen; Y is 4-phenylmalemimido or 3-phenylmaleimido; and Y' is methyl or hydrogen. It is preferred that the compound is present in about a 2.5-fold molar excess over the Hb concentration. The concentration of Hb is typically about 0.1 mM to about 3.0 mM, and most preferably about 0.5 mM; the concentration of the compound is typically about 0.25 mM to about 7.5 mM, and most preferably about 1.25 mM. Higher or lower concentrations of the components may be used. The reaction should be performed for about 0.25 to about 3 hours, and preferably about 1 hour, at room temperature, at pH about 6.5–8.5, and preferably neutral pH. The reaction may also be carried out at about 4° C. overnight if desired. The progress of the reaction as well as the subsequent purification may be performed as described above.

The hemoglobin composition (when m is about 3 to about 16) may be prepared by (a) reacting Hb with a thiolating agent such as iminothiolane, and (b) reacting the thiolated Hb with the compound having the formula:

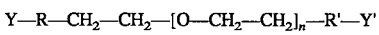

$$Y-R-CH_2-CH_2-[O-CH_2-CH_2]_n-R'-Y' \quad (Id)$$

wherein n is an integer from about 5 to about 200; R is carbamate, urea, or amide; R' is carbamate, urea, amide, or oxygen; Y is 4-phenylmalemimido or 3-phenylmaleimido; and Y' is methyl or hydrogen. For thiolation, the concentration of Hb is typically about 0.1 mM to about 3.0 mM, and most preferably about 0.5 mM; the concentration of the thiolating agent is about 5 to 20 fold molar excess over the concentration of Hb. The thiolating reaction is preferably performed for about 1 to 3 hours, and preferably 2 hours, at a pH of about 6.5–8.5, and preferably neutral pH. The number of sulfhydryl groups introduced onto Hb is a function of the concentration of the thiolating agent and the period of thiolation. The compound is then added to the reaction mixture preferably at about a 2-fold molar excess over the Hb concentration. Typical concentrations are about 0.2 mM to about 6.0 mM, and most preferably about 1.0 mM. Higher or lower concentrations of the compound may be used. The reaction should be performed for about 0.25 to about 3 hours, and preferably about 1 hour, at room temperature, at pH about 6.5–8.5, and preferably neutral pH. The reaction may also be carried out at about 4° C. overnight if desired. The progress of the reaction as well as the subsequent purification may be performed as described above.

The present invention also provides a pharmaceutical composition comprising any of the compositions above and a pharmaceutically acceptable carrier. Suitable carriers include but are not limited to various physiologically acceptable solutions known in the art such as saline solution, Ringer's solution, lactated Ringer's solution, Locke-Ringer's solution, Kreb's Ringer's solution, Hartmann's balanced saline solution, and heparinized sodium citrate acid dextrose solution. The pharmaceutical compositions also may comprise known plasma substitutes and plasma expanders. The pharmaceutical compositions of the present invention may be used as blood substitutes, and the like, and may be administered by conventional means including but not limited to transfusion and injection.

The present invention is described in the following Examples which are set forth to aid in the understanding of the invention, and should not be construed to limit in any way the invention as defined in the claims which follow thereafter.

EXAMPLE 1

Preparation of Maleated Para-Aminobenzoic Acid

Solution "A" was prepared by dissolving 42.6 grams of para-aminobenzoic acid in 300 ml acetone plus 50 ml of methyl alcohol. Solution "B" was prepared by dissolving 36.6 g of maleic anhydride in 100 ml acetone. Solution "B" was added to solution "A" in one shot at room temperature with stirring. The mixture was allowed to stir for one to two hours until a yellow precipitate was formed. The precipitate was then washed with fresh acetone and dried to yield approximately 62 grams of maleamidated benzoic acid.

EXAMPLE 2

Preparation of Para-Maleimidobenzoic Acid 62 grams of the maleamidated benzoic acid was mixed with 150 mls of acetic anhydride, 10.8 grams of anhydrous sodium acetate, and stirred at 50° C. for two hours followed by evaporation of volatiles under vacuum. The gummy residue was mixed and heated with one liter portion of water at 60°–70° C. for 2–2.5 hours resulting in a cream colored suspension of solids which were filtered, washed with fresh water, and dried overnight in a vacuum desiccator containing solid sodium hydroxide to yield 50 grams of para-maleimidobenzoic acid.

EXAMPLE 3

Preparation of Para-Maleimidobenzoylazide 43 grams of para-maleimidobenzoic acid, 30 mls of triethylamine and 47 mls of diphenylphosphoazide were added to 1.5 liters of toluene at room temperature and stirred for two days. At the end of this period, the reaction mixture was evaporated under reduced pressure (40°–50° C.) to an oily residue. This residue was dissolved in a minimum of warm chloroform and flash chromatographed over activated silica until the chloroform liquors were light yellow in color. Partial evaporation and cooling of the silica treated solution produced 22–25 grams of light-yellow needles (m.p. 131–132, with sudden evolution of nitrogen).

EXAMPLE 4

Preparation of p-Maleimidophenyl Isocyanate (PMPI)

25 grams of p-Maleimidobenzoylazide was dissolved in 1.0 liters of warm toluene and heated to reflux for 2 hours. At the end of this period, the reaction liquors were evaporated to dryness under vacuum and the residue recrystallized from chloroform/hexane to yield 20–23 grams of PMPI as bright yellow crystals (m.p. 121–123). Alternatively, PMPI may be obtained commercially from BioAffinity Systems, Inc. (Roscoe, Ill. USA).

EXAMPLE 5

Preparation of Bis-Maleimidophenyl Carbamate of Polyethylene Glycol 100 grams of polyethylene glycol (PEG) (MW2000) was azeotropically dried with toluene (1.5 liters) and cooled to room temperature under an atmosphere of nitrogen. To the dried PEG solution was added 23 gm PMPI and the solution was reheated to 30°–40° C. with stirring for 3 hours. At the end of this reaction period, the solution was filtered and concentrated under vacuum to about 300 ml total volume. To the concentrated toluene solution was added (with stirring) five volumes of anhydrous ethyl ether. The resulting yellow precipitate was filtered at the pump, redissolved in 500 mls of dry chloroform, filtered, re-precipitated with 5 volumes of ethyl ether, and dried to yield 100 grams of light yellow solid. Infrared spectra (KBr disc) revealed carbonyl contributed from the maleimido moiety at 1710 $CM^{-1}$ which was absent in a spectra of PEG. The compound was designated Bis-Mal-PEG 2000. Two PEG molecules were synthesized as described above, using PEG (MW 600) and PEG (MW 3400), and were designated as Bis-Mal-PEG 600 and Bis-Mal-PEG 3400, respectively.

EXAMPLE 6

Preparation of Alpha-Methoxy, Omega-4-Maleimidophenylcarbamate of PEG 25 grams of methoxy polyethylene glycol (MW 5000)(methoxy PEG-5000) was dissolved in 250 mls of toluene and refluxed with a Dean-Stark trap to remove water. To the dried solution was added 2.1 grams of PMPI as prepared in Example 4. The reaction was stirred overnight at room temperature, filtered and vacuum evaporated to a syrup. Ethyl ether was added to solidify the crude product. The resulting light yellow powder was dissolved in 500 ml of deionized water at room temperature, mixed with 1 gram of activated carbon and filtered. The haze-free yellow filtrate was extracted with 2×250 mls of chloroform which was dried with anhydrous calcium sulfate. The dried chloroform extract was concentrated and the desired product was precipitated as a light yellow powder upon addition of five volumes of ethyl ether. Filtration followed by drying yielded 20 grams of product showing carbonyl absorption in the infrared at 1710 $cm^{-1}$. The compound was designated Mal-Peg 5000.

EXAMPLE 7

Crosslinking of Hb With Bis Mal-PEG 2000

Figure 2A:
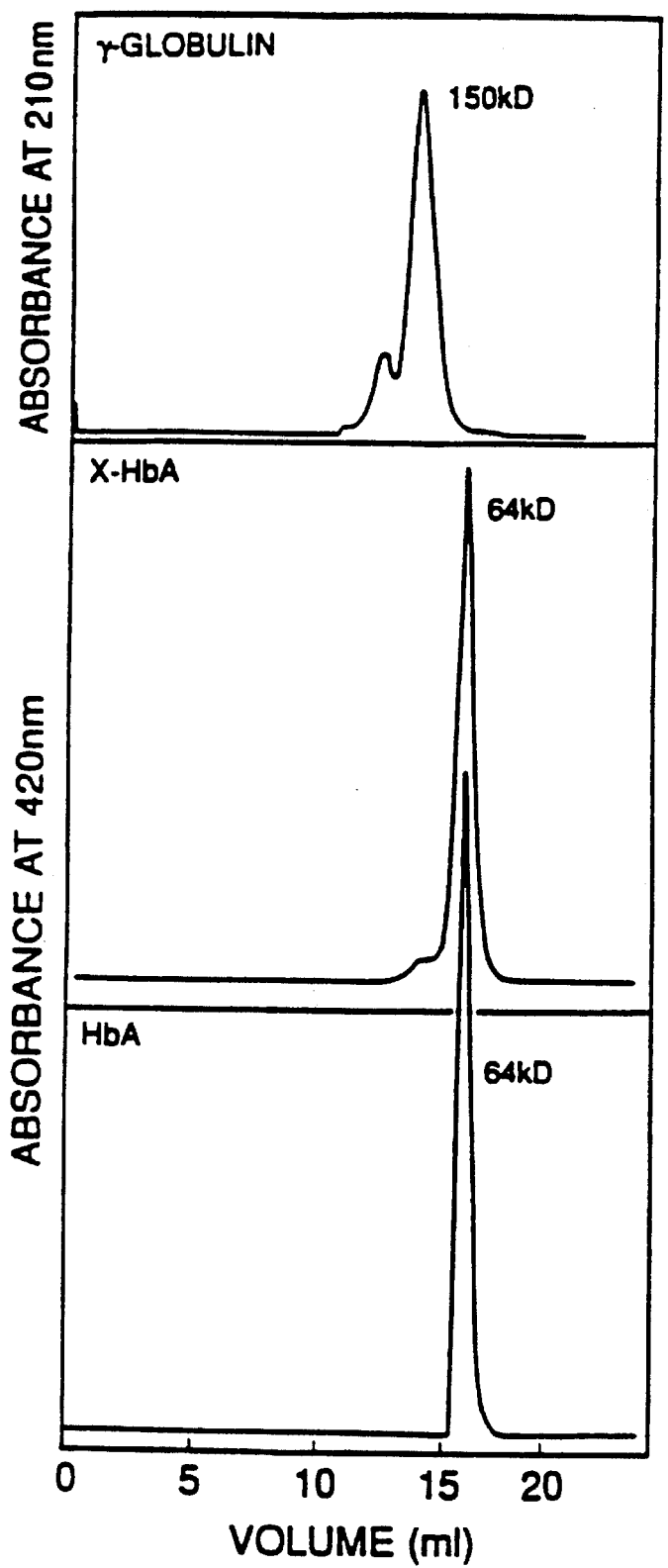
FIG. 2A represents the elution of samples on Superose-12 equilibrated and eluted with phosphate buffered saline, pH 7.4. The elution of γ-globulin, molecular weight 150,000 Kd is shown for comparison.
Figure 2B:
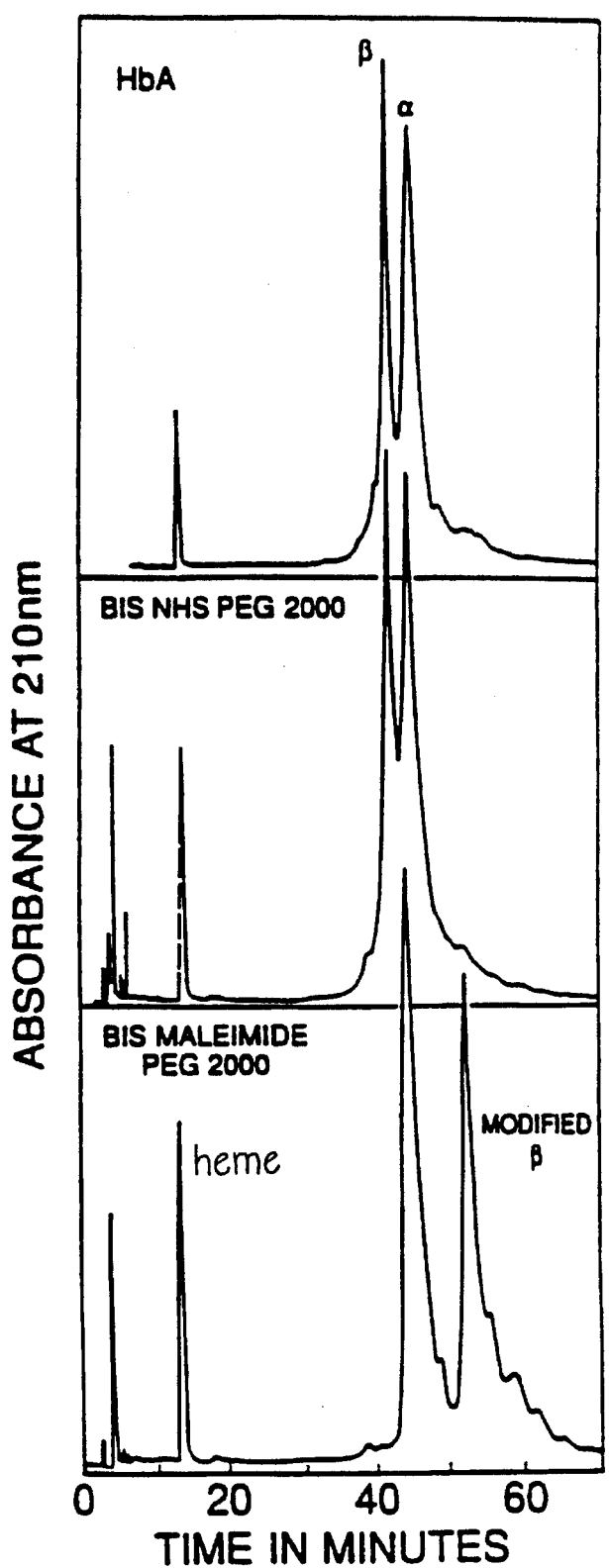
FIG. 2B represents the elution of the globin chains on RPHPLC columns. A Vydac C4 column was used for analysis. The column was equilibrated with 35% acetonitrile containing 0.1% trifluroacetic acid. The globin chains were eluted using a linear gradient of acetonitrile from 35 to 50 in 100 minutes.

HbA sample was purified from human erythrocyte lysates by DE-52 chromatography followed by CM-52 chromatography, and dialyzed extensively against phosphate buffered saline, pH 7.4. Two-fold molar excess of Bis-Mal-PEG 2000 (1 mM) was reacted with 0.5 mM of HbA at neutral pH and at room temperature for about 1 hour. Bis-succinimidyl acetyl polyethylene glycol (PEG MW 2000) was used as a control. FPLC analysis of the bifunctional reagent reacted Hb revealed that the only tetrameric form of Hb was present (see FIG. 2A). RPHPLC analysis of the globin chains demonstrated that all Bis-Mal-PEG 2000 modified the β-chain quantitatively, whereas the Bis NHS ester modified either the α- or β-chains (FIG. 2B).

Figure 3:
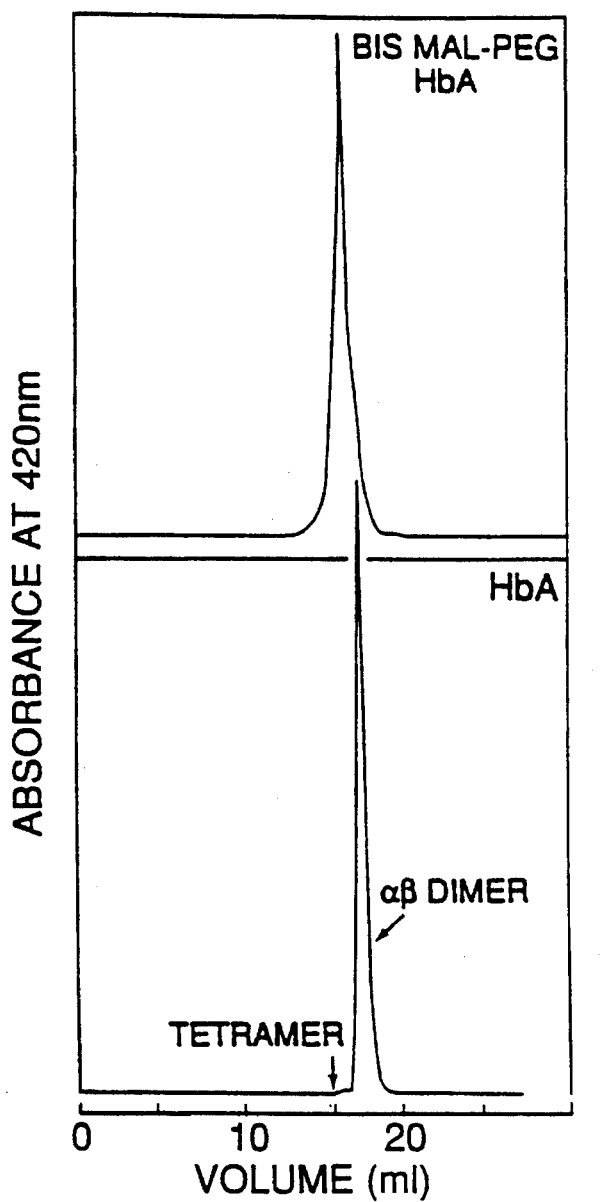
FIG. 3 represents the gel filtration of the Bis-Mal-PEG 2000 modified Hb on Superose-12 column equilibrated and eluted with bis tris acetate pH 7.0 containing 1M $MgCl_2$. The unmodified Hb dissociated into its αβ dimers and eluted as an apparent molecular mass of 32 Kd. The Bis-Mal-PEG 2000 modified protein eluted as a 64 Kd species.
Figure 3:
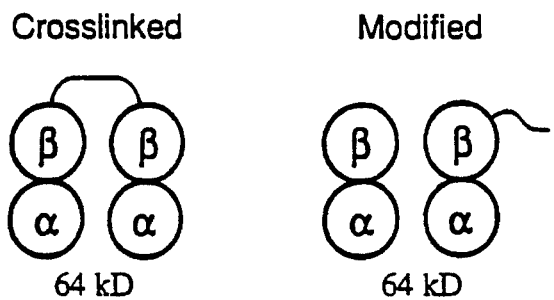

To determine whether Bis-Mal-PEG 2000 modified Hb by intramolecular crosslinking, the Bis-Mal-PEG 2000 modified Hb was subjected to gel filtration on a Superose-12 column equilibrated and eluted with bis tris acetate pH 7.0 containing 1M $MgCl_2$. The unmodified Hb was used as a control. As shown in FIG. 3, the unmodified Hb dissociates into αβ dimers and elutes with an apparent molecular mass of 32 Kd. The Bis-Mal-PEG 2000 modified. Hb elutes as 64 Kd species, which establishes that Bis-Mal-PEG 2000 introduced an intracrosslinking bridge between the two dimers of Hb. 100% of the Bis-Mal-PEG 2000 modified Hb was intracrosslinked and 0% was intercrosslinked.

Figure 4:
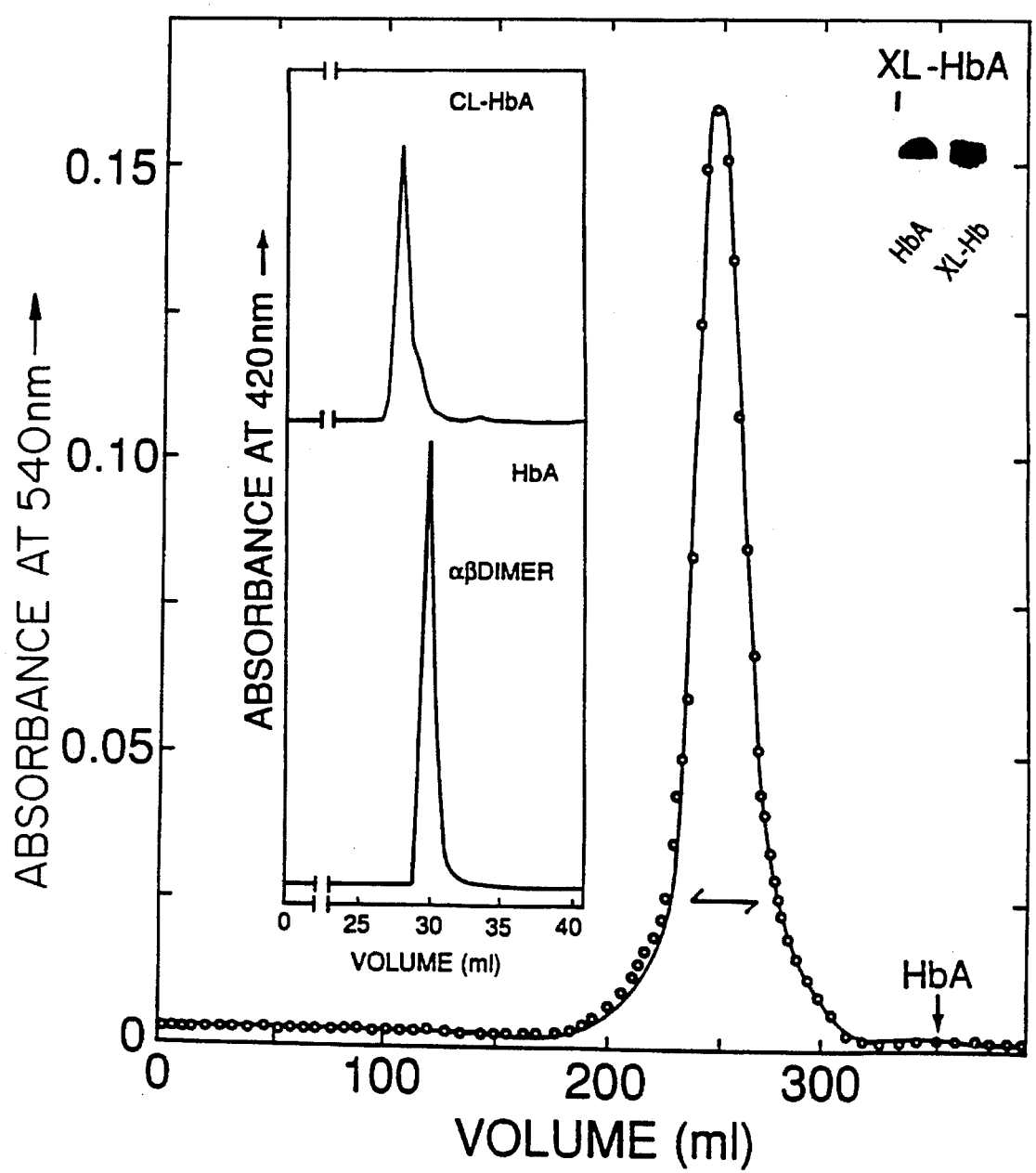
FIG. 4 represents the chromatography of Bis-Mal-PEG 2000 modified Hb on CM cellulose. A CM cellulose column (0.9×30 cm) was equilibrated with 10 mM potassium phosphate buffer (pH 6.0) containing 1 mM EDTA. A sample of Bis-Mal-PEG 2000 modified Hb (about 30 mg) was loaded onto the column. The protein was eluted with a linear gradient generated from 300 ml each of 10 mM potassium phosphate buffer pH 6.0 and 15 mM potassium phosphate buffer pH 8.0. The position of elution of HbA is marked for reference. The inset on the right shows the isoelectric focussing of the purified crossbridged sample. The inset on the left shows the elution of HbA and the purified sample on Superose-12 column equilibrated and eluted with bis tris acetate pH 7.0 containing 1M $MgCl_2$. The crosslinked eluted as a 64 Kd species demonstrating the intramolecular crossbridging of HbA by Bis-Mal-PEG 2000.

The Bis-Mal-PEG 2000 modified Hb was then purified on a CM-52 cellulose column (0.9×30 cm) equilibrated with 10 mM potassium phosphate buffer (pH 6.0) containing 1 mM EDTA. The protein was eluted with a linear gradient generated from 300 ml each of 10 mM potassium phosphate buffer pH 6.0 and 15 mM potassium phosphate buffer pH 8.0. The results are presented in FIG. 4. Consistent with the results of HPLC analysis, the Bis-Mal-PEG 2000 modified Hb did not contain any unmodified Hb. All materials eluted slightly ahead of the Hb peak. The isoelectric point of the CM-cellulose purified material was nearly the same as the parent unmodified Hb, demonstrating that the intramolecular crossbridging had little influence on the overall charge of the parent protein. The FPLC of the purified sample using 1M $MgCl_2$ as the eluent confirmed the intramolecular crosslinking.

The crosslinking site of the crosslinked β-chain isolated by RPHPLC was then mapped using trypic peptide mapping. The peptide missing was $\beta T_{10}$ that corresponds to the amino acid sequence 83 to 95. Given the site selectivity of the maleimide, Bis-Mal-PEG 2000 covalently linked the two Cys-93(β) residues of Hb.

Figure 5:
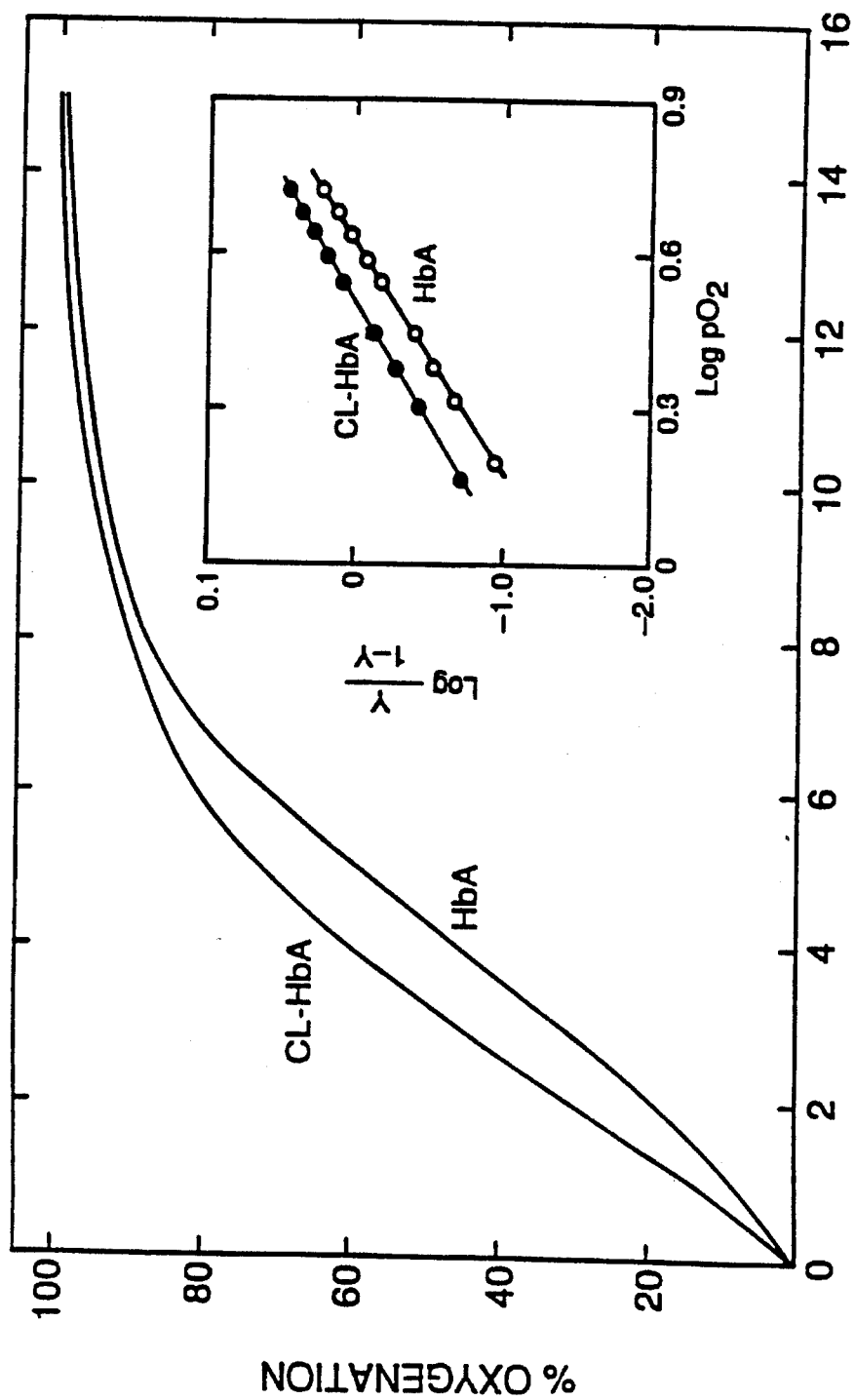
FIG. 5 represents the oxygen affinity of Bis-Mal-PEG 2000 modified Hb. The oxygen equilibrium was recorded using Hem O Scan. The inset depicts the Hill plots for the samples. The oxygen equilibrium curves were recorded at 37° C., in bis tris acetate pH 7.4.

The oxygen affinity of the Bis-Mal-PEG 2000 modified Hb in Bis tris acetate pH 7.4 at 37° C. was measured using Hem O Scan. Unmodified Hb was used as the control. The cooperactivity remained nearly the same as the control. The affinity of HbA was only slightly increased on intramolecular crosslinking as shown in FIG. 5. This very small reduction in oxygen affinity was unlike that previously reported for the monofunctional modification of Hb with N-ethyl maleimide (Riggs, A. *J. Biol. Chem.* 236:1948–1954 (1961)).

EXAMPLE 8

Crosslinking of Hb With Bis Mal-PEG 600 and Bis Mal-PEG 3400

Two-fold molar excess of Bis-Mal-PEG 600 and Bis-Mal-PEG 3400 each were reacted with 0.5 mM of HbA at neutral pH and at room temperature for about 1 hour. The relative distributions of uncrosslinked, and intra- verus intra-crosslinking for Bis-Mal-PEG 600 and Bis-Mal-PEG 3400, compared to Bis-Mal-PEG 2000 was as follows:

| Reagent | Uncrosslinked | Crosslinked Intra | Crosslinked Inter |
| --- | --- | --- | --- |
| PEG 600 | 0 | 80 | 20 |
| PEG 2000 | 0 | 100 | 0 |
| PEG 3400 | 20 | 75 | 5 |

In an attempt to increase the percentage of intermolecular crosslinked Hb, two-fold molar excess of Bis-Mal-PEG 600 was reacted with 2 mM of HbA at neutral pH and at room temperature for about 1 hour. At HbA concentration of 2 mM, the intermolecular crosslinking of Hb by Bis-Mal-PEG 600 increased to about 45–50%.

EXAMPLE 9

Thiolation of Hb Followed by Conjugation With Mal-PEG 5000

Figure 6:
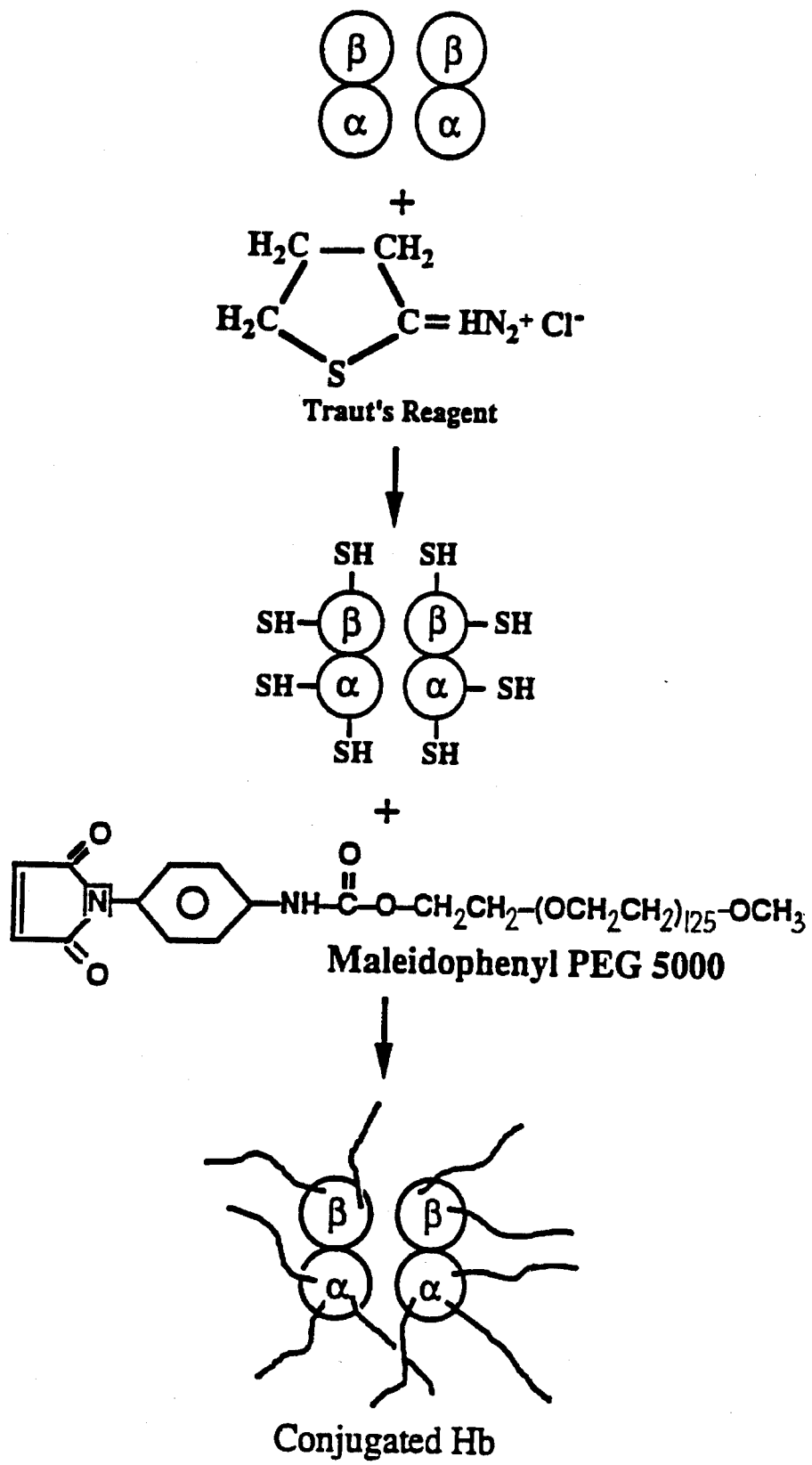
FIG. 6 represents a schematic diagram of the thiolation of Hb with Traut's Reagent followed by reaction with Mal-PEG 5000.
Figure 7:
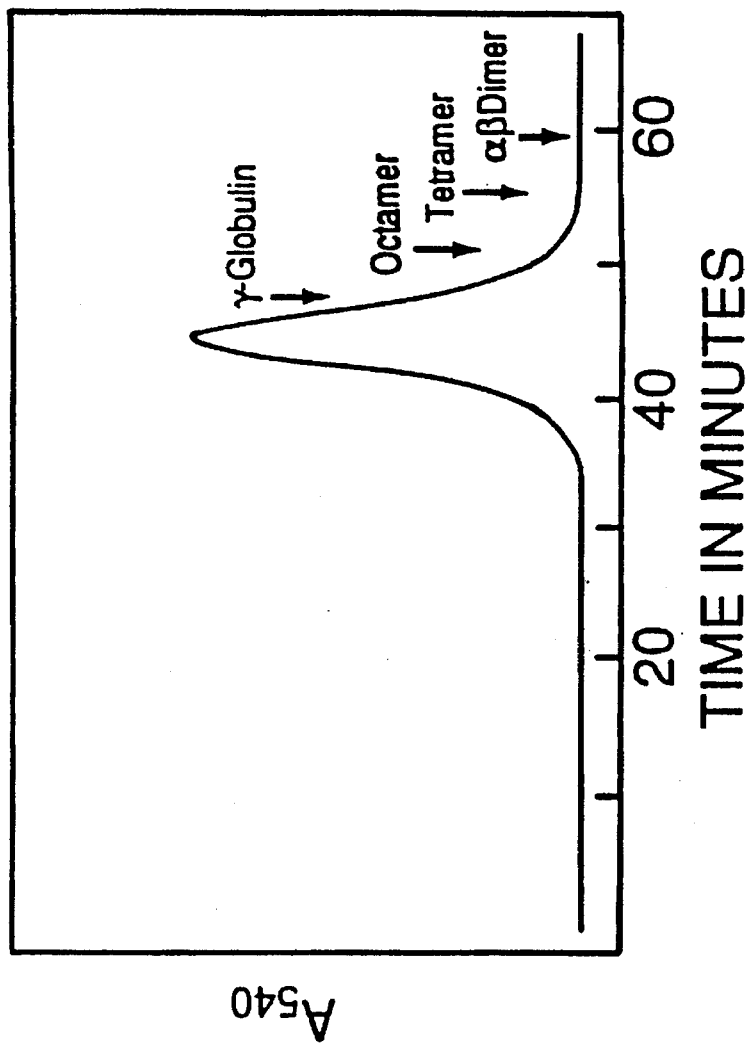
FIG. 7 represents the gel filtration of Mal-PEG 5000 on Superose-12 using phosphate buffered saline as the eluent.

Hb was thiolated using five fold molar excess of iminothiolane (Traut's Reagent)(Pierce Chemical Co.) as shown in FIG. 6. The reaction was carried out in phosphate buffer pH 7.4 at 4° C. overnight. A two fold excess of Mal-PEG 5000 was added to the reaction mixture, and the reaction was allowed to proceed for three hours in the cold. The results are presented in FIG. 7. The product formed had an apparent molecular weight of 200 kd or higher. The oxygen affinity of the Hb conjugate was only slightly lower than that of the parent Hb molecule. As a control, Hb without prior thiolation was reacted with five fold excess of Mal-PEG 5000. The product formed had an apparent molecular mass of about 128 Kd.

All publications mentioned hereinabove are hereby incorporated in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. An intra-crosslinked hemoglobin composition having the formula:

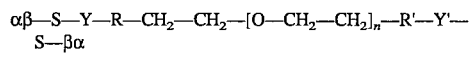

wherein n is an integer from about 5 to about 200; R and R' are carbamate, urea, or amide; and Y and Y' are 4-phenylsuccinimido or 3-phenylsuccinimido.

2. The composition of claim 1, wherein Y and Y' are 4-phenylsuccinimido.

3. The composition of claim 2, wherein R and R' are carbamate.

4. The composition of claim 2, wherein n is 13.

5. The composition of claim 2, wherein n is 45.

6. The composition of claim 2, wherein n is 75.

7. An inter-crosslinked hemoglobin composition having the formula:

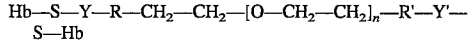

wherein n is an integer from about 5 to about 13; R and R' are carbamate, urea, or amide; and Y and Y' are 4-phenylsuccinimido or 3-phenylsuccinimido.

8. The composition of claim 7, wherein Y and Y' are 4-phenylsuccinimido.

9. The composition of claim 8, wherein R and R' are carbamate.

10. The composition of claim 9, wherein n is 13.

11. A hemoglobin composition having the formula:

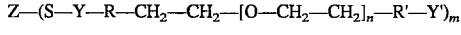

wherein n is an integer from about 5 to about 200; m is an integer from about 2 to about 16; R is carbamate, urea, or amide; R' is carbamate, urea, amide, or oxygen; Y is 4-phenylsuccinimido or 3-phenylsuccinimido; Y' is methyl or hydrogen; and Z is Hb or an αβ dimer of Hb.

12. The composition of claim 11, wherein Y is 4-phenylsuccinimido and Y' is methyl.

13. The composition of claim 12, wherein R is carbamate and R' is oxygen.

14. The composition of claim 13, wherein n is 125.

15. The composition of claim 14, wherein m is 8.

* * * * *